United States Patent [19]
Boyce

[11] Patent Number: 5,222,599
[45] Date of Patent: Jun. 29, 1993

[54] NEEDLE/SYRINGE AND BLOOD CONTAINMENT DEVICE

[76] Inventor: Donald R. Boyce, 1049 71 St., Brooklyn, N.Y. 11228-1214

[21] Appl. No.: 883,568

[22] Filed: May 15, 1992

[51] Int. Cl.⁵ .................... B65D 25/00; B65D 25/54
[52] U.S. Cl. ................... 206/366; 206/45.31; 220/504; 220/23.83
[58] Field of Search .................... 206/366, 365

[56] References Cited

U.S. PATENT DOCUMENTS

| | | | |
|---|---|---|---|
| 4,580,688 | 4/1986 | Harris et al. | 206/366 X |
| 4,714,168 | 12/1987 | Johnson et al. | 206/366 X |
| 4,715,498 | 12/1987 | Hanifl | 206/366 |
| 4,930,631 | 6/1990 | Bruno | 206/366 |
| 4,989,307 | 2/1991 | Sharpe et al. | 206/366 X |

Primary Examiner—William I. Price
Attorney, Agent, or Firm—Michael I. Kroll

[57] ABSTRACT

A containment device for hypodermic needles/syringes and the like is provided which consists of a shuttle container having an entry port. A mechanism is for inserting the hypodermic needles/syringes and the like one-way through the entry port and into the shuttle container. A structure is for sealing off the entry port when the shuttle container is full, so that the shuttle container can be properly disposed of. A storage receptacle is for holding a plurality of the shuttle containers therein when empty and when full.

12 Claims, 2 Drawing Sheets

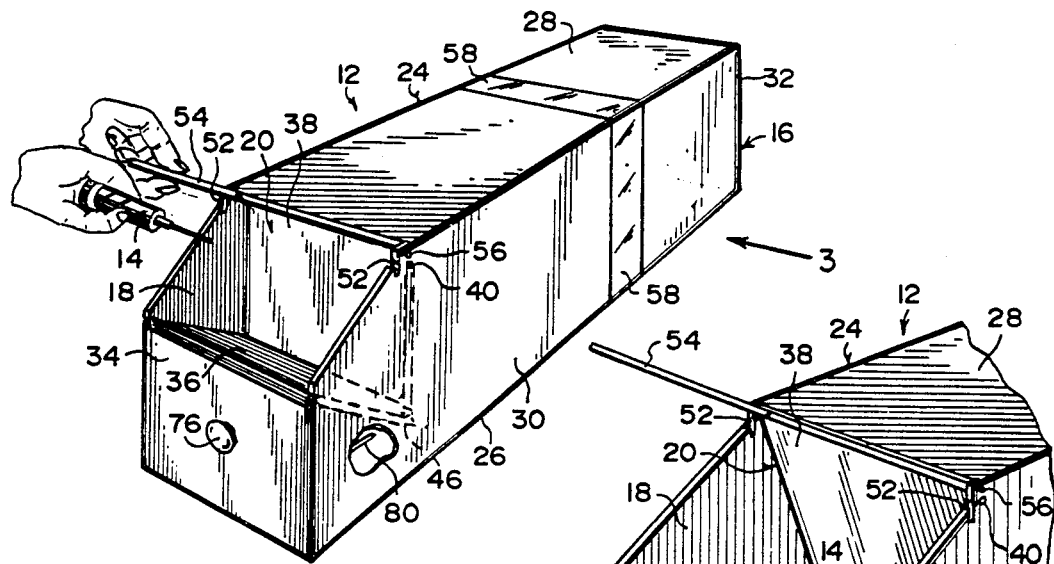
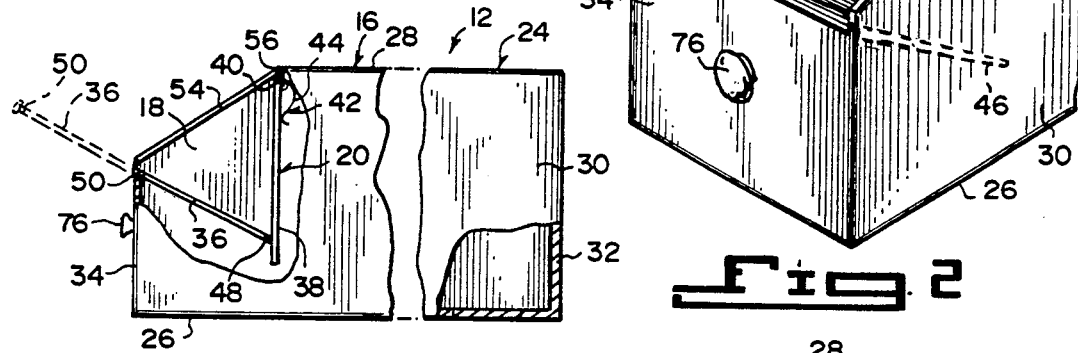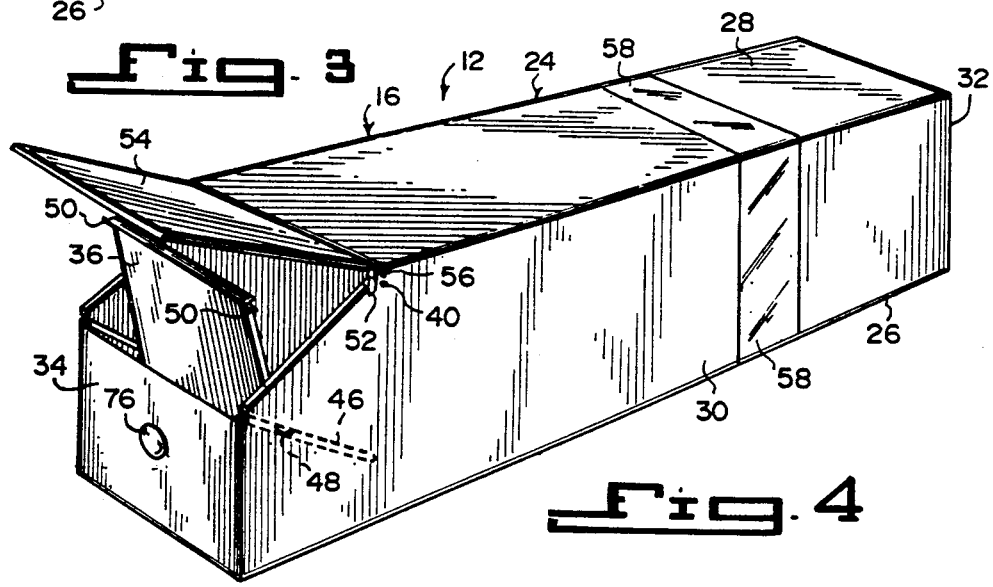

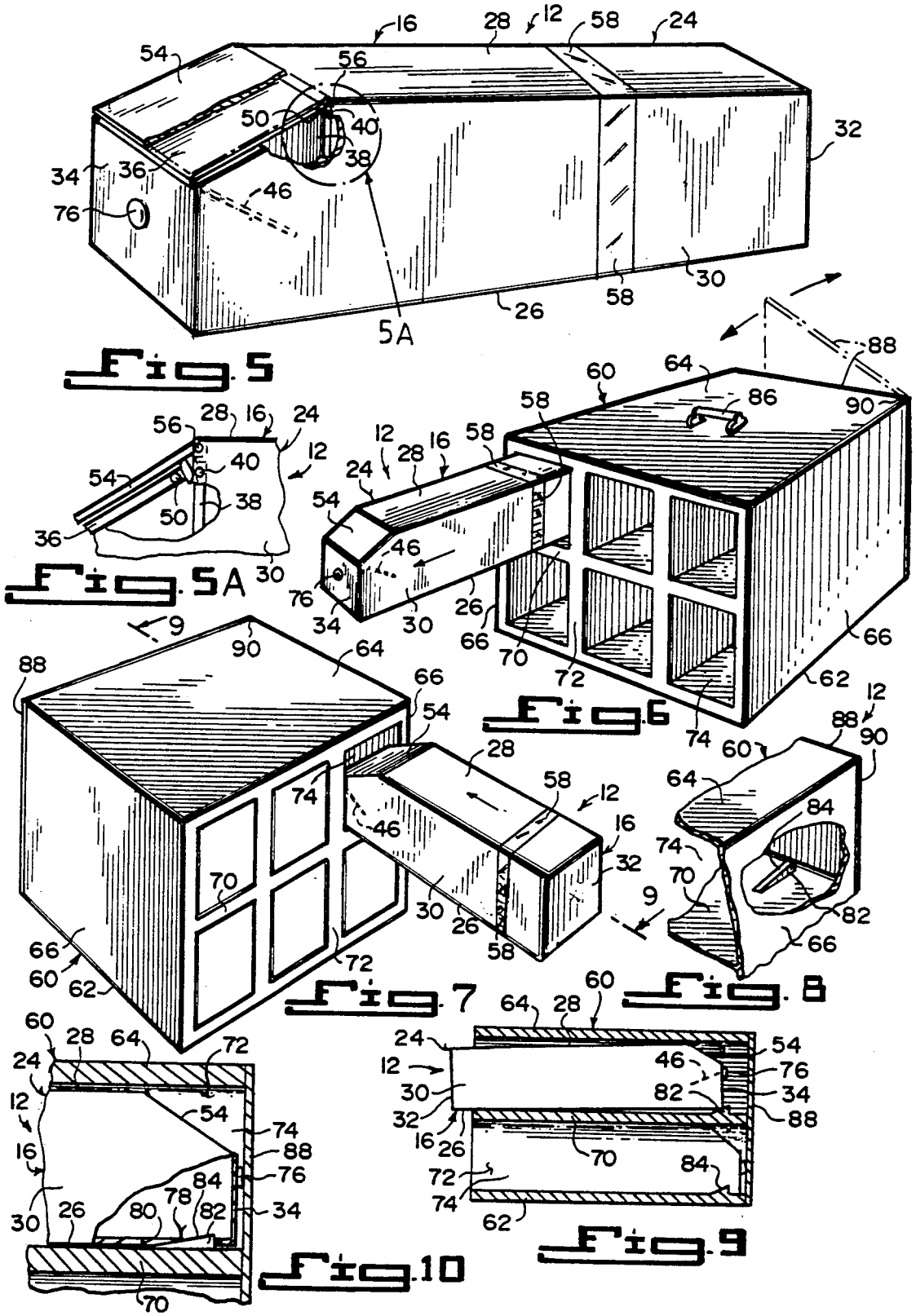

NEEDLE/SYRINGE AND BLOOD CONTAINMENT DEVICE

BACKGROUND OF THE INVENTION

1. Field of the Invention

The instant invention relates generally to holding apparatuses and more specifically it relates to a needle/syringe and blood containment device.

2. Description of the Prior Art

Numerous holding apparatuses have been provided in prior art that are adapted to retain various types of medical tools that are used by a significant portion of the medical population. While these units may be suitable for the particular purpose to which they address, they would not be as suitable for the purposes of the present invention as heretofore described.

SUMMARY OF THE INVENTION

A primary object of the present invention is to provide a needle/syringe and blood containment device that will overcome the shortcomings of the prior art devices.

Another object is to provide a needle/syringe and blood containment device that allows for the immediate disposal out of a hospital environment of hypodermic needles, syringes and angiocaths that are used for injections, IV therapy and medication administration.

An additional object is to provide a needle/syringe and blood containment device that will best serve the needs of paramedics, flight crews, visiting nurses, doctors on call, insurance/preemployment physical personnel and diabetics.

A further object is to provide a needle/syringe and blood containment device that is simple and easy to use.

A still further object is to provide a needle/syringe and blood containment device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURE

FIG. 1 is a perspective view of a shuttle container showing a hypodermic syringe with needle ready to be inserted within an entry port.

FIG. 2 is an enlarged perspective view of the front portion of the shuttle container showing the hypodermic syringe with needle entering therein.

FIG. 3 is a side view taken in direction of arrow 3 in FIG. 1 with parts broken away.

FIG. 4 is a perspective view of the shuttle container showing the shelf partially pulled out from the entry port.

FIG. 5 is a perspective view of the shuttle container with parts broken away showing the shelf in its retained position over the entry port.

FIG. 5A is an enlarged side view of a portion of the shuttle container as indicated by arrow 5A in FIG. 5.

FIG. 6 is a perspective view of a storage receptacle with one empty shuttle container therein.

FIG. 7 is a perspective view of the storage receptacle showing the last full shuttle container ready to be retained therein.

FIG. 8 is a perspective view of an upper rear portion of the storage receptacle showing one tapered mounting member therein.

FIG. 9 is a cross sectional view taken along 9—9 in FIG. 7.

FIG. 10 is an enlarged cross sectional view of the upper rear portion of the storage receptacle showing the shuttle container retained therein.

DETAILED DESCRIPTION OF THE PREFERRED EMBODIMENTS

Turning now descriptively to the drawings, in which similar reference characters denote similar elements throughout the several views, the Figures illustrate a containment device 12 for hypodermic needles/syringes and the like 14 which consists of a shuttle container 16 having an entry port 18. A mechanism 20 is for inserting the hypodermic needles/syringes and the like 14 one-way through the entry port 18 and into the shuttle container 16. A structure 22 is for sealing off the entry port 18 when the shuttle container 16 is full, so that the shuttle container 16 can be properly disposed of.

The shuttle container 16 is a rectangular shaped box 24 with the entry port 18 angularly positioned upwardly from one end thereof. The rectangular shaped box 24 includes a bottom wall 26, a top wall 28, a pair of long side walls 30, each extending upwardly between the bottom wall 26 and the top wall 28, a narrow rear wall 32 and a narrow front wall 34 with the entry port 18 angularly positioned between the short front wall 34 and the top wall 28.

The one-way inserting mechanism 20 consists of a shelf 36 angularly positioned downwardly from the front wall 34 in the entry port 18 to extend into the rectangular shaped box 24, so as to guide the hypodermic needles/syringes and the like 14 therein. An internal drop plate 38 is hinged at 40 to the to wall 28 at the entry port 18, so as to hang down into the rectangular shaped box 24 to the bottom edge of the shelf 36. A mechanism 42 is for normally biasing the bottom of the drop plate 38 against the bottom edge of the shelf 36, so that the hypodermic needles/syringes and the like 14 can only go one-way into the rectangular shaped box 24.

The normally biasing mechanism 42 is a coil spring 44 located at the hinge 40 of the internal drip plate 38, so as to press the bottom portion of the drop plate 38 against the bottom edge of the shelf 36, thereby only allowing the internal drop plate 38 to swing inwardly therefrom.

The sealing off structure 22 includes each side wall 30 having an internal channel 46 angularly positioned downwardly from the front wall 34 in the entry port 18 to extend into the rectangular shaped box 24. A first pair of pins 48 are provided with each extending from one lower side edge of the shelf 36 to ride within the internal channel 46 in the side wall 30. A second pair of pins 50 are also provided, with each extending from one upper side edge of the shelf 36 to also ride within the internal channel 46, in the side wall 30. Each side wall 30 also has a notch 52 located at the entry port 18 near the top wall 28 thereof. When the rectangular shaped box 24 is full, the shelf 36 can be pulled partly outwardly from the internal channels 46 and flipped over with the second pair of pins 50 engaging with the notches 52 to retain the shelf 36 over the entry port 18.

An external door 54 is hinged at 56 to the top wall 28 at the entry port 18 above the hinge 40 of the internal drop plate 38. The external door 54 normally covers the entry port 18 and must be lifted when the hypodermic needles/syringes and the like 14 are deposited therein and when the shelf 36 is placed into its retained position over the entry port 18.

The rectangular shaped box 24 further contains a transparent window 58 located in the side walls 30 and the top wall 28 to visually indicate when the rectangular shaped box 24 is full, so that the entry port 18 may be sealed.

A storage receptacle 60, as shown in FIGS. 6 through 10 is for holding a plurality of the shuttle containers 16 therein when empty and when full. The storage receptacle 60 includes a bottom wall 62, a top wall 64 and a pair of side walls 66, each extending upwardly between the bottom wall 62 and the top wall 64. A horizontal partition wall 70 extends parallel between the bottom wall 62 and the top wall 64. At least one vertical partition wall 72 extends parallel between the side walls 66, so as to form a plurality of compartments 74, for holding the plurality of shuttle containers 16 therein.

Each shuttle container 16 includes a knob 76 affixed to the front wall 34, so that the rectangular shaped box 24, when empty, can be inserted into and pulled out of one of the compartments 74 of the storage receptacle 60.

An apparatus 78 is for retaining each rectangular shaped box 24, when full within each compartment 74 of the storage receptacle 60. Each retaining apparatus 78 consists of the bottom wall 26 of the rectangular shaped box 24 having a slot 80 therein located near the front wall 34. A tapered male locking member 82 is attached to an inner surface of the bottom wall 62/horizontal partition wall 70 of the storage receptacle 60 within one compartment 74 and is located near the rear wall 68. The male locking member 82 has a gradual top inclined surface 84 with a wide portion facing the rear wall 68. When the rectangular box 24 is full, it can be inserted within the compartment 74 with the front wall 34 going in first until the slot 80 engages with and is retained by the tapered male locking member 82.

The storage receptacle 60 further includes a handle 86 affixed to the top wall 64, so that the storage receptacle 60 can be carried therefrom. A rear access door 88 is hinged at 90 to one of the side walls 66, so as to make disposal of the full shuttle containers 16 possible and the storage receptacle 60 reusable again.

LIST OF REFERENCE NUMBERS

12: containment device
14: hypodermic needle/syringe and the like
16: shuttle container
18: entry port in 16
20: one-way inserting mechanism
22: sealing off structure
24: rectangular shaped box for 16
26: bottom wall of 24
28: top wall of 24
30: long side wall of 24
32: narrow rear wall of 24
34: narrow front wall of 24
36: shelf
38: internal drop plate
40: hinge for 38
42: normally biasing mechanism
44: coil spring for 42
46: internal channel in 30
48: pin on 36
50: pin on 36
52: notch in 30
54: external door
56: hinge for 54
58: transparent window
60: storage receptacle
62: bottom wall of 60
64: top wall of 60
66: side wall of 60
70: horizontal partition wall of 60
72: vertical partition wall of 60
74: compartment in 60
76: knob on 34
78: retaining apparatus
80: slot in 26
82: tapered male locking member
84: gradual top inclined surface of 82
86: handle for 60
88: rear access door
90: hinge for 88

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A containment device for hypodermic needles/syringes which comprises:
    a) a shuttle container having an entry port, said shuttle container is a rectangular shaped box with the entry port angularly positioned upwardly from one end thereof, said rectangular shaped box includes a bottom wall a top wall a pair of long side walls each extending upwardly between said bottom wall and said top wall a narrow rear wall a narrow front wall with the entry port angularly positioned between said short front wall and said top wall;
    b) means for inserting the hypodermic needles/syringes one-way through the entry port and into said shuttle container, said one-way inserting means includes a shelf angularly positioned downwardly from said front wall in the entry port to extend into said rectangular shaped box so as to guide the hypodermic needles/syringes therein, an internal drop plate hinged to said top wall at the entry port so as to hang down into said rectangular shaped box to the bottom edge of said shelf means for normally biasing the bottom of said drop plate against the bottom edge of said shelf so that the hypodermic needles/syringes can only go one-way into said rectangular shaped box; and c) means for sealing off the entry port when said shuttle container is full so that said shuttle container can be properly disposed of.

2. A containment device as recited in claim 1, wherein said normally biasing means is a coil spring located at the hinge of said internal drop plate, so as to press the bottom portion of said drop plate against the bottom edge of said shelf thereby only allowing said internal drop plate to swing inwardly therefrom.

3. A containment device as recited in claim 2, wherein said sealing off means includes:
a) each said side wall having an internal channel angularly positioned downwardly from said front wall in the entry port to extend into said rectangular shaped box;
b) a first pair of pins, each extending from one lower side edge of said shelf to ride within the internal channel in said side wall;
c) a second pair of pins, each extending from one upper side edge of said shelf to also ride within the internal channel in said side wall; and
d) each said side wall also having a notch located at the entry port near said top wall thereof, so that when said rectangular shaped box is full said shelf can be pulled partly outwardly from said internal channels and flipped over with said second pair of pins engaging with said notches to retain said shelf over the entry port.

4. A containment device as recited in claim 3, further including an external door hinged to said top wall at the entry port above the hinge of said internal drop plate, whereby said external door normally covers the entry port and must be lifted when the hypodermic needles/syringes are deposited therein and when said shelf is placed into its retained position over the entry port.

5. A containment device as recited in claim 4, wherein said rectangular shaped box further includes a transparent window located in said side walls and said top wall to visually indicate when said rectangular shaped box is full, so that the entry port may be sealed.

6. A containment device as recited in claim 5, further including a storage receptacle for holding a plurality of said shuttle containers therein when empty and when full.

7. A containment device as recited in claim 6, wherein said storage receptacle includes:
a) a bottom wall;
b) a top wall;
c) a pair of side walls, each extending upwardly between said bottom wall and said top wall;
d) a horizontal partition wall extending parallel between said bottom wall and said top wall; and
e) at least one vertical partition wall extending parallel between said side walls, so as to form a plurality of compartments for holding the plurality of shuttle containers therein.

8. A containment device as recited in claim 7, wherein each said shuttle container includes a knob affixed to said front wall, so that said rectangular shaped box when empty can be inserted into and pulled out of one of the compartments of said storage receptacle.

9. A containment device as recited in claim 8, further including means for retaining each said rectangular shaped box when full within each compartment of said storage receptacle.

10. A containment device as recited in claim 9, wherein each said retaining means includes:
a) said bottom wall of said rectangular box having a slot therein located near said front wall; and
b) a tapered male locking member attached to an inner surface of said bottom wall/said horizontal partition of said storage receptacle within one compartment and located near said rear wall, said male locking member having a gradual top inclined surface with a wide portion facing said rear wall, so that when said rectangular box is full, it can be inserted within the compartment with said front wall going in first until said slot engages with and is retained by said tapered male locking member.

11. A containment device as recited in claim 10, wherein said storage receptacle further includes a handle affixed to said top wall, so that said storage receptacle can be carried therefrom.

12. A containment device as recited in claim 11, wherein said storage receptacle further includes a rear access door hinged to one of said side walls, so as to make disposal of said full shuttle containers possible and said storage receptacle reusable again.

* * * * *